(12) United States Patent
Leighton et al.

(10) Patent No.: US 9,604,407 B2
(45) Date of Patent: Mar. 28, 2017

(54) 3D PRINTING TECHNIQUES FOR CREATING TISSUE ENGINEERING SCAFFOLDS

(71) Applicant: XEROX CORPORATION, Norwalk, CT (US)

(72) Inventors: Roger Leighton, Hilton, NY (US); David Allen Mantell, Rochester, NY (US)

(73) Assignee: XEROX CORPORATION, Norwalk, CT (US)

( * ) Notice: Subject to any disclaimer, the term of this patent is extended or adjusted under 35 U.S.C. 154(b) by 711 days.

(21) Appl. No.: 14/095,202

(22) Filed: Dec. 3, 2013

(65) Prior Publication Data
US 2015/0151487 A1    Jun. 4, 2015

(51) Int. Cl.
| B29C 67/00 | (2006.01) |
| B33Y 10/00 | (2015.01) |
| C12M 3/00 | (2006.01) |
| C12M 1/12 | (2006.01) |

(52) U.S. Cl.
CPC ...... B29C 67/0059 (2013.01); B29C 67/0092 (2013.01); B33Y 10/00 (2014.12); *C12M 25/14* (2013.01)

(58) Field of Classification Search
CPC . B29C 67/0059; B29C 67/0092; C12M 25/14
USPC .................. 264/108, 250, 255, 308
See application file for complete search history.

(56) References Cited

U.S. PATENT DOCUMENTS

| 5,518,680 | A | * | 5/1996 | Cima | A61F 2/022 156/272.8 |
| 5,997,795 | A | * | 12/1999 | Danforth | B29C 33/3842 264/219 |
| 7,968,026 | B1 | * | 6/2011 | Teoh | A61L 27/18 264/113 |
| 8,197,743 | B2 | * | 6/2012 | Wicker | B29C 67/0055 264/233 |
| 2005/0276791 | A1 | | 12/2005 | Hansford et al. | |

(Continued)

FOREIGN PATENT DOCUMENTS

| CN | 103919629 A | 7/2014 |
| EP | 1855618 A2 | 11/2007 |

(Continued)

OTHER PUBLICATIONS

Fedorovich et al. Three-Dimensional Fiber Deposition of Cell-Laden, Viable, Patterned Constructs for Bone Tissue Printing. Tissue Engineering A, vol. 14 No. 1 (2008) 127-133.*

(Continued)

*Primary Examiner* — Atul P. Khare
(74) *Attorney, Agent, or Firm* — MH2 Technology Law Group LLP

(57) ABSTRACT

A method for printing a three-dimensional tissue scaffold. An embodiment can include printing a first layer of scaffold fiber with a printer onto a base gel substrate; and disposing a first gel layer over the printed first layer. Another embodiment can include printing a first and second sacrificial fiber with a printer onto a base gel substrate; printing a first scaffold fiber between the first and second sacrificial fiber to form a printed first layer; and disposing a first gel layer over the printed first layer.

12 Claims, 3 Drawing Sheets

(56) References Cited

U.S. PATENT DOCUMENTS

| | | | |
|---|---|---|---|
| 2006/0105011 A1* | 5/2006 | Sun | B29C 67/0059 424/422 |
| 2008/0208358 A1* | 8/2008 | Bellamkonda | A61L 27/16 623/23.72 |
| 2009/0208577 A1* | 8/2009 | Xu | A61L 27/38 424/484 |
| 2010/0211172 A1* | 8/2010 | Bellamkonda | A61B 5/0031 623/11.11 |
| 2011/0212501 A1* | 9/2011 | Yoo | A61L 27/54 435/174 |
| 2012/0040461 A1* | 2/2012 | Beachley | A61L 27/48 435/396 |
| 2012/0089239 A1 | 4/2012 | Sentgeorge et al. | |
| 2012/0329156 A1* | 12/2012 | Cho | A61L 27/14 435/397 |

FOREIGN PATENT DOCUMENTS

| | | | | |
|---|---|---|---|---|
| EP | 2546588 A2 | 1/2013 | | |
| SG | WO 2013172788 A1 * | 11/2013 | | A61L 27/52 |
| WO | 2006/096791 A2 | 9/2006 | | |
| WO | 2009/102484 A2 | 8/2009 | | |
| WO | 2014/039427 A1 | 3/2014 | | |

OTHER PUBLICATIONS

Search Report dated May 1, 2015 from Great Britain Applications No. 1420675.9, pp. 1-4.

* cited by examiner

3D PRINTING TECHNIQUES FOR CREATING TISSUE ENGINEERING SCAFFOLDS

FIELD OF THE EMBODIMENTS

The present teachings relate to the field of tissue engineering scaffolds and more particularly to methods for printing a tissue scaffold.

BACKGROUND OF THE EMBODIMENTS

Scaffolds are vital components in tissue engineering. The success of functional tissue or organ regeneration relies on the development of suitable scaffolds to direct three-dimensional growth. Normal cell proliferation in nature is a precisely controlled series of events that inherently relies on spatial and temporal organization. Culturing cells in two dimensions, i.e., on a glass or polystyrene substrate, overlooks many parameters known to be important for accurately reproducing cell and tissue physiology. Such two-dimensional growth is not an accurate representation of the extracellular matrix found in native tissue. Many complex biological responses, such as receptor expression, transcriptional expression, and cellular migration, are known to differ significantly in two-dimensional growth conditions versus native conditions.

Current techniques seek to create scaffold structures that resemble those found in nature. Scaffolds are three dimensional (3D) structures that possess the proper shape, size, architecture, and physical properties to provide structural support for cell attachment and subsequent tissue development. Structural properties, such as macroscopic shape (architecture), pore size, porosity, pore interconnectivity, surface area, surface chemistry, and mechanical properties, are critical considerations in the design of scaffolds for tissue engineering, particularly in the regeneration of large and complex tissues. Typically, a viable scaffold must have high porosity, appropriate stiffness, high degree of reproducible precision, and appropriate pore sizes for target-specific tissue development. Scaffolds are usually created with biodegradable polymers and hydrogels, and typically degrade over time as the tissue grows around it. As the tissue starts building its own extracellular matrix to support its structure and function, the scaffold degrades to avoid inhibiting further tissue growth.

Various fabrication techniques have been developed to create suitable scaffolds, including melt molding, fiber bonding, spin casting, solvent casting and particulate leaching. Although scaffolds produced from these conventional techniques can address individual issues (e.g., architecture, pore size, or porosity), there is still a need for constructing scaffolds in a way that can address multiple structural issues and can meet the structural, mechanical, and nutritional requirements necessary for cellular growth.

SUMMARY OF THE EMBODIMENTS

The following presents a simplified summary in order to provide a basic understanding of some aspects of one or more embodiments of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

In an embodiment, a method for printing a three-dimensional tissue scaffold includes printing a first layer of scaffold fiber with a printer onto a base gel substrate; and disposing a first gel layer over the printed first layer.

In another embodiment a method for printing a three-dimensional tissue scaffold can include printing a first and second sacrificial fiber with a printer onto a base gel layer; printing a first scaffold fiber between the first and second sacrificial fibers to form a printed first layer; and disposing a first gel layer over the printed first layer.

BRIEF DESCRIPTION OF THE DRAWINGS

The accompanying drawings, which are incorporated in and constitute a part of this specification, illustrate embodiments of the present teachings and together with the description, serve to explain principles of the disclosure. In the figures.

It should be noted that some details of the figures have been simplified and are drawn to facilitate understanding of the present teachings rather than to maintain strict structural accuracy, detail, and scale.

DESCRIPTION OF THE EMBODIMENTS

Reference will now be made in detail to exemplary embodiments of the present teachings, examples of which are illustrated in the accompanying drawings. Wherever possible, the same reference numbers will be used throughout the drawings to refer to the same or like parts.

As used herein, unless otherwise specified, a "printer" encompasses any apparatus that performs a deposition of material onto a substrate. While the present teachings are described herein with reference to a printer that prints a molten polymer, specifically a molten biodegradable polymer, it will be understood that any material that is capable of forming a tissue scaffold and is capable of being dispensed from a printer may advantageously incorporate an embodiment of the present teachings. Additionally, for purposes of the present invention, the word "ink" is used to refer to any material that is dispensed by the printer, and can include any compound or mixture that falls within the scope of the present teachings. Further, unless otherwise specified, a "molten" material includes a material that is in a non-solid form, for example liquid or semi-viscous.

An embodiment of the present teachings includes printing a first layer of scaffold fiber with a printer onto a base gel substrate and disposing a first gel layer over the printed first layer to form a tissue scaffold. This approach to building a tissue scaffold creates alternating printed scaffold fiber layers and gel layers, where the gel layers act as a soft support for the next printed scaffold fiber layer, thus creating a layered scaffold.

Another embodiment of the present teachings includes printing a first and second sacrificial fiber with a printer onto a base gel substrate; printing a first scaffold fiber between the first and second sacrificial fiber to form a printed first layer; and disposing a first gel layer over the printed first layer. This approach to building a tissue scaffold creates "containment walls" with the sacrificial fibers to reduce the width of the scaffold fiber in the printed first layer, and helps increase the overall porosity of the tissue scaffold.

Figure 1:
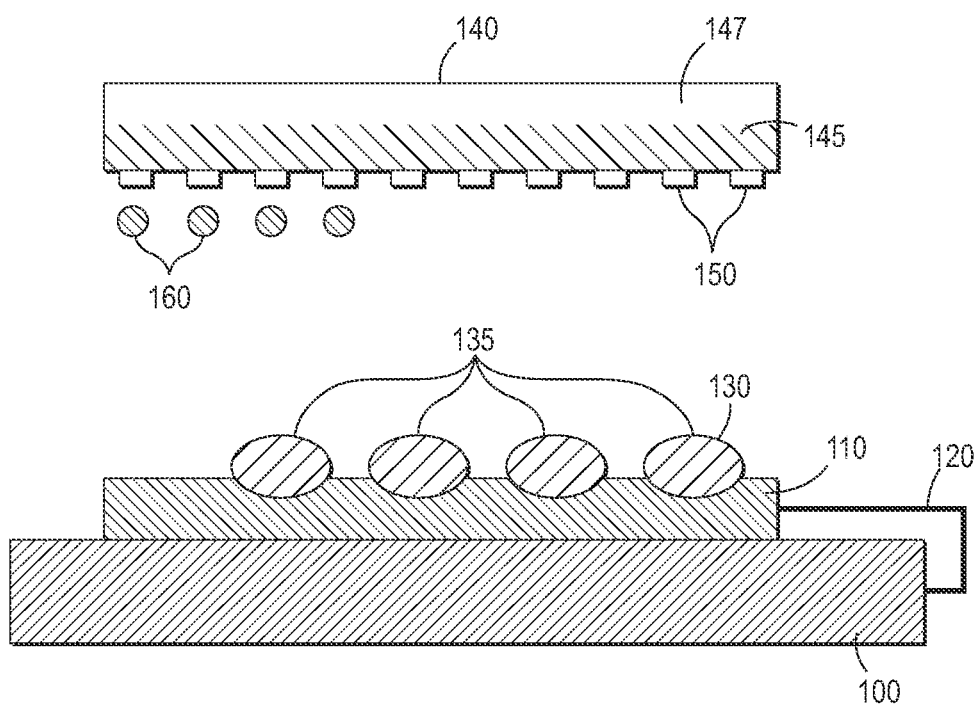
FIG. 1 is a cross section of a first embodiment of the present teachings for printing a three-dimensional tissue scaffold.
Figure 2A:
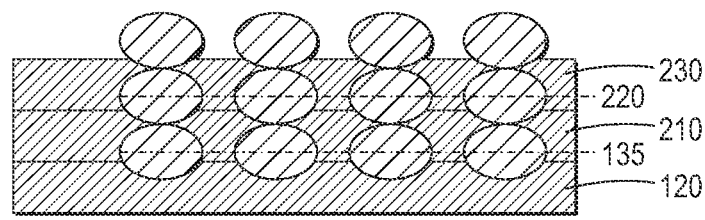
FIG. 2A is another cross section of a first embodiment of the present teachings for printing a three-dimensional tissue scaffold.
Figure 2B:
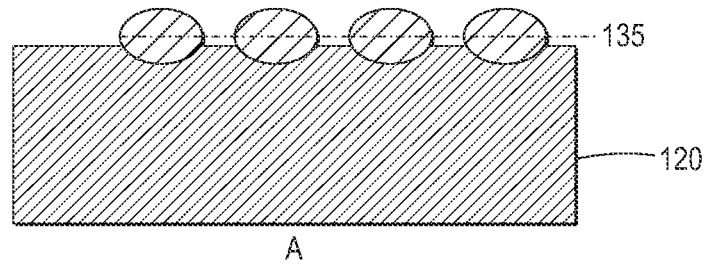
FIG. 2B is a further cross section of a first embodiment of the present teachings for printing a three-dimensional tissue scaffold.
Figure 2B:
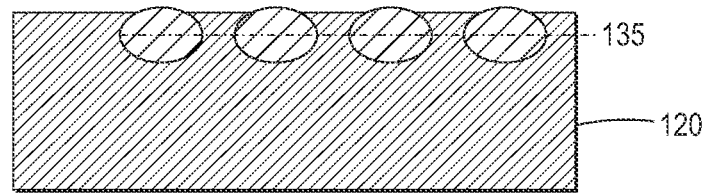
Figure 2B:
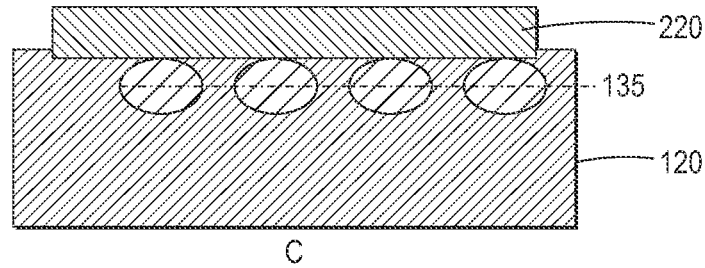
Figure 2B:
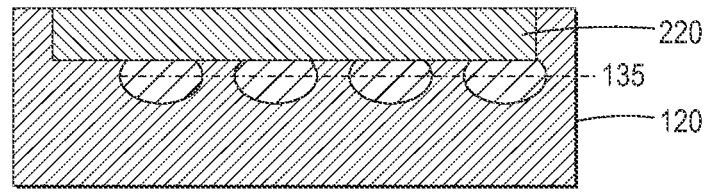
Figure 3:
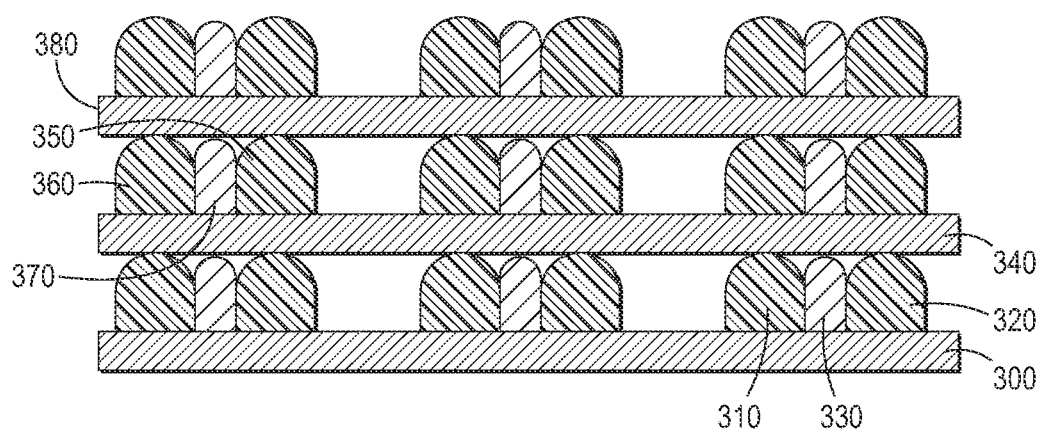
FIG. 3 is a cross section of a second embodiment of the present teachings for printing a three-dimensional tissue scaffold.

Embodiments of the present teachings can include methods and in-process structures which can be formed during embodiments of the present teachings, for example as depicted in FIGS. 1-3 and described in the accompanying text.

FIG. 1 depicts a base gel substrate 120 and a printed first layer 135. The base gel substrate 120 includes a base gel layer 110 disposed over a porous substrate 100. The porous substrate 100 can be any sterile material capable of supporting nutrient and waste transport, such as sterile filter paper. The base gel layer 110 can include hydrogels, naturally-derived degradable polymers, synthetic degradable polymers, or combinations thereof. The base gel layer 110 can further include extracellular matrix proteins.

Examples of synthetic degradable polymers include, but are not limited to, poly(glycolic acid) (PGA), poly(lactic acid) (PLA), poly(ε-caprolactone) (PCL), polyurethanes, poly(ortho esters) (POE), poly(anhydrides), polyvinyl alcohol (PVA), tyrosinederived polycarbonates, copolymers thereof, and combinations thereof. Naturally-derived degradable polymers include, but are not limited to, collagen, chitosan, fibrin, glycosaminoglycans, silk fibroin, agarose, alginate, starch, and combinations thereof. Non-limiting examples of hydrogels include poly(ethylene oxide) (PEO), poly(vinyl alcohol) (PVA), poly(acrylic acid) (PAA), agarose, alginate, chitosan, collagen, fibrin, gelatin, hyaluronic acid (HA), or mixtures thereof.

In a specific embodiment, the base gel layer includes Geltrex® (Life Technologies Corp., Carlsbad, Calif.) or Matrigel® (BD Biosciences, Billerica, Mass.). In another specific embodiment, the gel layer can include poly(lactic acid) and/or copolymers thereof.

A printer 140 is used to deposit a first layer of scaffold fiber 130 onto the base gel substrate 120 to form a printed first layer 135, as depicted in FIG. 1. It will be apparent to one of ordinary skill in the art that the structures such as printer 140, printer nozzle 150, etc. depicted in the figures represent schematic illustrations and that other structures or elements can be added or existing structures or elements can be removed or modified. The scaffold fiber 130 can be any biodegradable polymer suitable for building a tissue scaffold, including naturally-derived degradable polymers or synthetic degradable polymers. Preferably, the scaffold fiber 130 is different than the base gel layer 110. Examples of synthetic degradable polymers include, but are not limited to, poly(glycolic acid) (PGA), poly(lactic acid) (PLA), poly(ε-caprolactone) (PCL), polyurethanes, poly(ortho esters) (POE), poly(anhydrides), polyvinyl alcohol (PVA), tyrosine derived polycarbonates, copolymers thereof, and combinations thereof. Exemplary naturally-derived degradable polymers include, but are not limited to, collagen, chitosan, fibrin, glycosaminoglycans, silk fibroin, agarose, alginate, starch, and combinations thereof. In an embodiment, the scaffold fiber is a tyrosine-derived polycarbonate.

During printing, droplets 160 of a solution of the biodegradable polymer can be ejected from a printer nozzle 150 onto the base gel substrate 120 to form a first printed layer 135 made of scaffold fibers 130. The base gel substrate 120 can sit on a moveable platen 90. Printer 140 may be, for example, a drop-on-demand (DOD) ink jet printer. Ink, for example molten biodegradable polymer in solution, can be ejected as a plurality of droplets 160 through the nozzles 150 using a transducer such as a piezoelectric element which deflects a diaphragm as known in the art. In the case of a DOD printer, for example, the droplets 160 can be simultaneously ejected from the plurality of nozzles 150 as individual droplets; however, the droplets 160 coalesce together to create contiguous scaffold fibers 130 so as to form a first printed layer 135. In an embodiment, the droplets 160 can be ejected from the printer nozzles 150 at a firing frequency ranging from about 20 kHz to about 43 kHz.

During printing, the jetting process necessary to create a scaffold fiber is the combination of jetting frequency and pile height buildup. Jetted molten droplets 160 of the biodegradable polymer can have a viscosity ranging from about 6 to about 20 cP, a surface tension ranging from about 20 to about 40 dynes/cm, and/or a size ranging from about 14 to about 25 picoliters,. The thermal mass of the droplet 160 allows the droplet to land on the gel layers and locally melt the gel layers so that the local melting cradles the droplets, thus reducing or preventing polymer splatter. As the droplets arrive at the gel interface (i.e., every 50 μsec or 20 kHz), each new drop fuses into the previous drop and coalesces. This allows contiguous deposition of droplets 160 to form a scaffold fiber 130.

The scaffold fiber 130 diameter is a function of the rate of platen movement under the printer head. For example, a platen speed of 70 mm/sec (i.e., 35 um in 0.5 ms) allows the surface energy of the droplets 160 to coalesce together to form a scaffold fiber 130. As a further example, ten 14 picoliter droplets, jetted in a single x, y coordinate, can form a fiber diameter of 60 μm. The platen speed should be continuous so as to allow formation of contiguous fibers, and fast enough that a fiber is created versus forming a coalescing sphere of polymer.

The printer 140 may be a printer other than a DOD ink jet printer, such as an extrusion printer, a solid ink printer, or a printer which uses other ink printing technology. In an embodiment, the printer can include a reservoir 147 which contains a supply of material 145 and, in this embodiment, a plurality of nozzles 150 through which the material 145 is printed or extruded under pressure. In the case of an extrusion printer, for example, droplets 160 depict extruded material 145 to create contiguous polymer fibers so as to form a first printed layer 135. In an aspect, the extruded material 145 is molten biodegradable polymer.

Additionally, the speed of platen movement, which affects the fiber diameter being generated, can be further varied depending on the desired diameter. The slower the platen rate, the higher the pile height buildup and therefore, the wider the fiber diameter. One of ordinary skill in the art can control the firing frequency and speed of platen movement to control the degree of contiguity in the scaffold fiber, which affects the tensile strength. The more contiguous the fiber, the higher the tensile strength.

After the first layer of scaffold fiber is printed, a first gel layer 210 can be disposed over the printed first layer 135, as depicted in FIG. 2A. Subsequently, a second layer of scaffold fiber can be printed with a printer over the first gel layer 210 to form a printed second layer 220. Thereafter, a second gel layer 230 can be disposed over the printed second layer 220. This process can be repeated layer by layer until the desired architecture is achieved. In an aspect, the printed second layer 220 can be parallel, perpendicular, or oriented crosswise in relation to the printed first layer 135. That is, the printed second layer 22 can be disposed parallel, perpendicularly, diagonally or transversely over the printed first layer 135 to create a lattice structure layer by layer.

Optionally, the printed layers may be heated so as to sink the scaffold fibers into the underlying gel layer in a controlled manner before the next layer is disposed. For example, in an aspect, the printed first layer 135 can be heated, causing the base gel layer 120 to locally melt underneath the scaffold fibers, which allows the printed first layer 135 to wholly or partially sink into the base gel layer 120 before the first gel layer 210 is disposed. Likewise, the printed second layer 220 can be heated, causing the first gel layer 210 to locally melt underneath the scaffold fibers, which allows the printed second layer 220 to wholly or partially sink into the first gel layer 210 before the second gel layer 230 is disposed. In an embodiment, a laser can be used to selectively heat the printed layers. For example, a laser can be used to increase overall scaffold strength by applying the laser to crosswise junctions between two strands of scaffold fiber in the printed layer (e.g., where two strands cross each other), and locally melting and fusing one strand of scaffold fiber to another strand at the junction, as well as increase the polymer strand strength. The remelt will allow the polymer strands to realign.

Alternatively, the printed layers may be heated so as to sink the scaffold fibers into a single base gel layer sufficiently thick to encompass the desired height of the final scaffold. Each printed layer is heated and sunk into the base gel layer before the next scaffold fiber layer is printed. Construction of such an exemplary layered scaffold is depicted in FIG. 2B. In a) a printed first layer 135 is disposed over the base gel layer 120. In b) the printed first layer 135 is selectively heated to locally melt underneath the scaffold fibers, allowing the printed first layer 135 to wholly or partially sink into the base gel layer 120. In c) the printed second layer 220 is disposed over the printed first layer. In d) the printed second layer 220 is selectively heated to locally melt underneath the scaffold fibers, allowing the printed second layer 220 to wholly or partially sink into the base gel layer 120. This process can be repeated layer by layer until the desired architecture is achieved. At a desired time, the water soluble base gel layer can be dissolved in a manner suitable for its composition as known in the art, resulting in a final scaffold where the printed layers are joined together to form a desired architecture.

Another embodiment of the present teachings is depicted in the cross section of FIG. 3. As depicted in FIG. 3, a first sacrificial fiber 310 and a second sacrificial fiber 320 are printed onto a base gel layer 300. A first scaffold fiber 330 is then printed in between the first and second sacrificial fibers 310, 320 to form a printed first layer. Subsequently, a first gel layer 340 is disposed over the printed first layer. Thereafter, a third and fourth sacrificial fiber 350, 360 can be printed onto the first gel layer 340, and a second scaffold fiber 370 is printed in between the third and fourth sacrificial fibers 350, 360 to form a printed second layer. Subsequently, a second gel layer 380 is disposed over the printed second layer. This process can be repeated layer by layer until the desired architecture is achieved. At a desired time, the sacrificial fibers are dissolved in a manner suitable for its composition as known in the art.

By creating "containment walls" with the sacrificial fibers, a thinner scaffold fiber can be generated. The "containment walls" constrain the scaffold fiber in a trapped geometry to prevent gravity from changing the aspect ratio as the polymer. Further, the gel layers help support the printed scaffold fibers and improve the overall porosity of the final scaffold.

In an embodiment, each of the sacrificial fibers has a width of from about 20 µm to about 90 µm, for example from about 70 µm to about 90 µm. In an aspect, the space between the sacrificial fibers ranges from about 10 µm to about 50, for example from about 30 µm to about 50 µm.

The sacrificial fibers can be a hydrogel or a synthetic degradable polymer. Examples of synthethic degradable polymers include, but are not limited to, poly(glycolic acid) (PGA), poly(lactic acid) (PLA), poly(ϵ-caprolactone) (PCL), polyurethanes, poly(ortho esters) (POE), poly(anhydrides), copolymers thereof, and combinations thereof. Non-limiting examples of hydrogels include poly(ethylene oxide) (PEO), poly(vinyl alcohol) (PVA), poly(acrylic acid) (PAA), agarose, alginate, chitosan, collagen, fibrin, gelatin, hyaluronic acid (HA), or mixtures thereof. Preferably, the sacrificial fibers are not the same as the scaffold fibers. In a specific embodiment, the sacrificial fiber is a hydrogel, or poly(lactic acid) and/or copolymers thereof.

The scaffold fibers can be any biodegradable polymer suitable for building a tissue scaffold, including naturally-derived degradable polymers or synthetic degradable polymers. Examples of synthetic degradable polymers include, but are not limited to, poly(glycolic acid) (PGA), poly(lactic acid) (PLA), poly(ϵ-caprolactone) (PCL), polyurethanes, poly(ortho esters) (POE), poly(anhydrides), polyvinyl alcohol (PVA), tyrosine-derived polycarbonates, copolymers thereof, and combinations thereof. Naturally-derived degradable polymers include, but are not limited to, collagen, chitosan, fibrin, glycosaminoglycans, silk fibroin, agarose, alginate, starch, and combinations thereof. In an embodiment, the scaffold fiber is a tyrosine-derived polycarbonate.

The gel layers can include hydrogels, naturally-derived degradable polymers, synthetic degradable polymers, or combinations thereof. The gel layers can further include extracellular matrix proteins. Examples of synthetic degradable polymers include, but are not limited to, poly(glycolic acid) (PGA), poly(lactic acid) (PLA), poly(ϵ-caprolactone) (PCL), polyurethanes, poly(ortho esters) (POE), poly(anhydrides), copolymers thereof, and combinations thereof. Naturally-derived degradable polymers include, but are not limited to, collagen, chitosan, fibrin, glycosaminoglycans, silk fibroin, agarose, alginate, starch, and combinations thereof. Non-limiting examples of hydrogels include poly (ethylene oxide) (PEO), poly(vinyl alcohol) (PVA), poly (acrylic acid) (PAA), agarose, alginate, chitosan, collagen, fibrin, gelatin, hyaluronic acid (HA), or mixtures thereof.

In a specific embodiment, the gel layers include Geltrex® (Life Technologies Corp., Carlsbad, Calif.) or Matrigel® (BD Biosciences, Billerica, Mass.). In another specific embodiment, the gel layers include poly(lactic acid) and/or copolymers thereof.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "about" indicates that the value listed may be somewhat altered, as long as the alteration does not result in nonconformance of the process or structure to the illustrated embodiment. Finally, "exemplary" indicates the description is used as an example, rather than implying that it is an ideal. Other embodiments of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. Terms such as "on," "higher," "lower," "over," "top," and "under" are defined with respect to the conventional plane or working surface being on the top surface of the workpiece, regardless of the orientation of the workpiece.

The invention claimed is:

1. A method for printing a three-dimensional tissue scaffold, the method comprising:

printing a layer of scaffold fibers with a printer onto a base gel substrate;

heating the printed layer to locally melt the underlying gel so that scaffold fibers of the heated layer sink wholly or partially into the melted gel;

disposing a gel layer over the sunk fibers; and repeating the printing, heating, and disposing steps multiple times over the gel layer to form successive layers of gel comprising wholly or partially sunk scaffold fibers until a desired architecture of the tissue scaffold is formed.

2. The method of claim 1, wherein said printing of the layers of scaffold fibers comprises ejecting a plurality of droplets of a solution of biodegradable polymer from at least one nozzle of the printer.

3. The method of claim 2, wherein the plurality of droplets have a viscosity ranging from about 6 to about 20 cP.

4. The method of claim 2, wherein the plurality of droplets have a surface tension ranging from about 20 to about 40 dynes/cm.

5. The method of claim 2, wherein the plurality of droplets have a size ranging from about 14 to about 25 picoliters.

6. The method of claim 2, wherein the at least one printer nozzle ejects the plurality of droplets at a firing frequency ranging from about 20 kHz to about 43 kHz.

7. The method of claim 2, wherein the scaffold fibers comprise contiguous droplets of the biodegradable polymer.

8. The method of claim 1, wherein the base gel substrate is disposed over a porous substrate, the base gel substrate comprising a gel layer.

9. The method of claim 1, wherein each of the gel layers comprises hydrogels, naturally-derived degradable polymers, synthetic degradable polymers, or combinations thereof.

10. The method of claim 9, wherein the synthetic degradable polymers are selected from the group consisting of poly(glycolic acid) (PGA), poly(lactic acid) (PLA), poly(s-caprolactone) (PCL), polyurethanes, poly(ortho esters) (POE), poly(anhydrides), polyvinyl alcohol (PVA), tyrosine-derived polycarbonates, copolymers thereof, and combinations thereof.

11. The method of claim 9, wherein the hydrogels comprise poly(ethylene oxide) (PEO), poly(vinyl alcohol) (PVA), poly(acrylic acid) (PAA), agarose, alginate, chitosan, collagen, fibrin, gelatin, hyaluronic acid (HA), or mixtures thereof.

12. The method of claim 1, further comprising dissolving the gel layers.

* * * * *